United States Patent [19]

Tsunekawa

[11] Patent Number: 4,542,527
[45] Date of Patent: Sep. 17, 1985

[54] IMAGE PROCESSING DEVICE FOR CONTINUOUSLY EXTRACTING FEATURES OF SMALL REGIONS OF AN IMAGE

[75] Inventor: Shou Tsunekawa, Yokohama, Japan

[73] Assignee: Tokyo Shibaura Denki Kabushiki Kaisha, Kawasaki, Japan

[21] Appl. No.: 494,254

[22] Filed: May 13, 1983

[30] Foreign Application Priority Data

May 17, 1982 [JP] Japan .................................. 57-82669
May 17, 1982 [JP] Japan .................................. 57-82671

[51] Int. Cl.⁴ .............................................. G06K 9/36
[52] U.S. Cl. ......................................... 382/52; 382/27
[58] Field of Search ..................................... 382/50-54, 382/27; 358/282, 284

[56] References Cited

U.S. PATENT DOCUMENTS 4,162,481 7/1979 DuVall .................................. 382/52
4,408,343 10/1983 Neill et al. ............................ 382/52

Primary Examiner—Leo H. Boudreau
Assistant Examiner—Joseph Mancuso
Attorney, Agent, or Firm—Oblon, Fisher, Spivak, McClelland & Maier

[57] ABSTRACT

An image processing device which processes a small region of a predetermined number (m×n) of picture elements in a two-dimensionally scanned image and successively obtaining accumulated output of picture element data of a new small region containing a new picture element each time the new picture element data is read out. The sum of data of n consecutive picture elements of each row in an array of (M×N) picture elements is obtained, and is updated every time a new picture element of the corresponding row is read. The accumulated sum of the picture element data of a small area having (m×n) picture elements is obtained, and is updated every time new picture element data is read, thereby obtaining the accumulated sum of new (m×n) picture element data.

7 Claims, 6 Drawing Figures

IMAGE PROCESSING DEVICE FOR CONTINUOUSLY EXTRACTING FEATURES OF SMALL REGIONS OF AN IMAGE

BACKGROUND OF THE INVENTION

The present invention relates to an image processing device and, more particularly, to an image processing device arranged to effectively extract the features of small areas of an image.

When the surface of an article is inspected for stains, flaws or defects, there is often performed such an image processing as picks up the surface of the article by a television camera and measures the density or the number of defects in a region of a predetermined area of the image. In such a conventional image processing method, in order to shorten the processing time, the entire region of the image is fixedly divided into a plurality of non-overlapping regions, and the image processing is performed for each divided region. The purpose of this image processing is to inspect whether the number of defects or the density in the predetermined area exceeds a predetermined value or threshold value or not. In the case that the image is fixedly divided into a plurality of small regions and the number of defects or the density of each small region is measured, the following problems will arise.

As shown in FIG. 1, it is assumed that an image 1 has (M×N) picture elements and is divided into small regions 2 each of (m×n) picture elements. It is also assumed that the image processing is performed to inspect the number of defects within the area of each divided region 2. For instance, it is also assumed that, a small region which contains more than two defects is rejected on the basis of an inspection criterion. On these assumptions, when defects 3 which are irregularly distributed are inspected, the situations shown in FIGS. 2A and 2B might occur. Namely, when the image 1 is fixedly divided into a plurality of small regions 2 without overlapping each others, there might occur a case where three defects 3a, 3b and 3c which are distributed within the area of small region 2 are contained in divided region 2 as shown in FIG. 2A, and a case where defects 3a, 3b and 3c are not contained in region 2 as shown in FIG. 2B. In these cases, the small region 2 of FIG. 2A is decided as being rejected, while the small region 2 of FIG. 2B is decided as being allowable. In other words, the presence of defects 3a, 3b and 3c contained in the area of a small region is ignored, thereby causing an inspection result to be in error. In order to overcome this problem in conventional image processing method, it is necessary to divide the entire region into a plurality of small regions overlapping each other in spite of consuming a lot of processing time.

SUMMARY OF THE INVENTION

It is an object of the present invention to provide an image processing device capable of accurately extracting the features containing inspected objects of small regions of an image in which the inspected objects are irregularly distributed, at a high speed.

In brief, the object of the present invention is achieved by forming a small region of a predetermined number of picture elements in a two-dimensionally scanned image and successively obtaining accumulated output of picture element data of a new small region containing a new picture element each time the new picture element data is read out.

According to the present invention, an image to be processed is regarded as having an array of (M×N) picture elements, and the picture elements are sequentially read out by two-dimensional scanning, where N designates the number of scanning lines, and M designates the number of picture elements per one scanning line. A small area is an array of (m×n) picture elements.

First memory means is provided which receives input picture element data sequentially read out, and has (M×n) stages to temporarily store (M×n) picture element data. The data of (M×n) picture elements thus temporarily stored are read out of the first memory means in the order of application of the (M×n) picture element data to the memory means. Second memory means of M stages is provided which temporarily stores data which are sequentially input thereto and causes the data thus stored to be sequentially read out in the input sequence. Further, first arithemetic operation circuit means is provided which performs an arithmetic operation of the input picture element data plus the output data of the second memory means minus the output data of the first memory means. The operation result is applied to the second memory means. The data sum of n consecutive picture elements of each row of the picture element array is stored in each stage of the second memory means. The data of each stage is updated every time a new picture element of the corresponding row is read out.

Further, there are provided third memory means for temporarily storing data and second arithmetic operation circuit means for effecting an arithmetic operation of the output data of the first arithmetic operation circuit plus the output data of the third memory means minus the output data of m(<M)-th stage of the second memory means. The output of the second arithmetic operation circuit means is input to the third memory means. The accumulated sum of the picture element data of a small region consisting of (m×n) picture elements is stored in the third memory means, and is updated every time new picture element data is read out, so that the accumulated data sums of the small regions each having (m×n) picture elements are successively obtained.

According to the present invention, the accumulated sum of the picture element data of a small area which has (m×n) picture elements is sequentially calculated every time a picture element is read out. Thus, the features of small regions can be accurately obtained at a high speed. The picture element data may be a two-valued signal or a multi-valued signal.

DETAILED DESCRIPTION OF THE PREFERRED EMBODIMENTS

Figure 3:
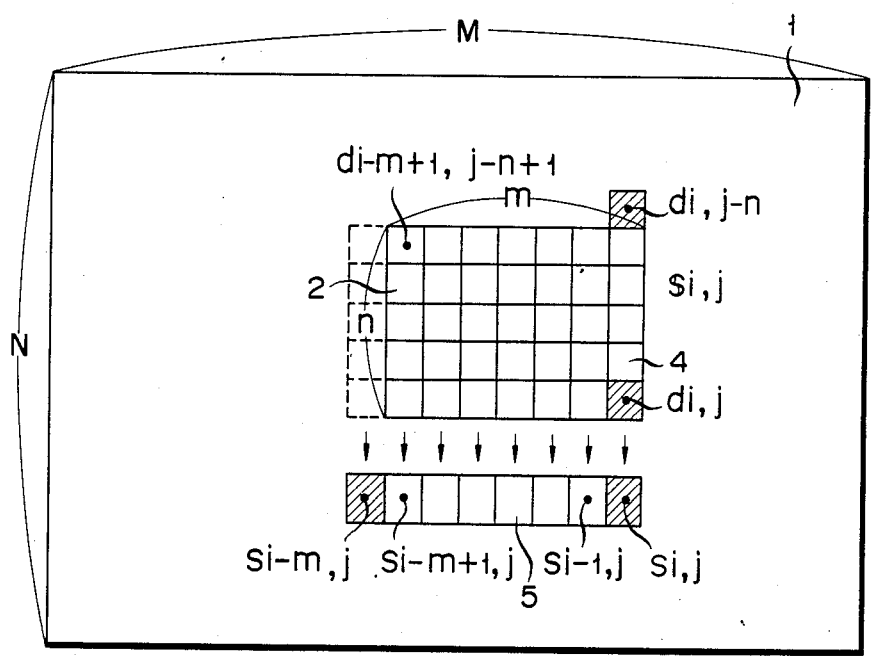
FIG. 3 is a diagram for describing the principle of an image processing according to the present invention.

FIG. 3 shows the principle of an image processing according to the present invention. In FIG. 3, reference numeral 1 designates an image which is obtained by two-dimensional scanning of a television camera, and has M picture elements in the scanning line (row) direction and N picture elements in the vertical (column) direction. In general, N is equal to the number of scanning lines. Reference numeral 2 designates a small region which has m picture elements in the row direction and n picture elements in the column direction, and 4 picture elements. Reference numeral 5 depicts the sum of the data of n picture elements in each column of small region 2.

It is assumed here that the accumulated sum $\mathcal{S}_{i-1,j}$ of data of (m×n) picture elements contained in small region 2 which is defined by positions (i−m, j−n+1) and (i−1, j) and the data sums $S_{i-m,j}$, $S_{i-m+1,j}$ to $S_{i-1,j}$ of data of n picture elements of m columns of small region 2 have been obtained. Then, it is also assumed that the data sum of a new small region which is displaced by one row rightwardly is calculated. In this case, data $d_{i,j}$ of a picture element at the position (i, j) is newly input, and the data sum $S_{i,j}$ of n picture elements from position (i, j) to position (i, j−n+1) of i-th row is calculated. $S_{i,j}$ is obtained by an arithmetic operation of the sum $S_{i,j-1}$ of data of picture elements from position (i, j−n) to (i, j−1) which has already been obtained minus picture element data $d_{i,j-n}$ at position (i, j−n) plus new input data $d_{i,j}$. In other words, $$S_{i,j} = S_{i,j-1} + d_{i,j} - d_{i,j-n}$$

The accumulated sum S of (m×n) picture element data in small region 2 which has i-row at its right end can be obtained as below.

$$\mathcal{S}_{i,j} = \mathcal{S}_{i-1,j} + S_{i,j} - S_{i-m,j}$$

Figure 1:
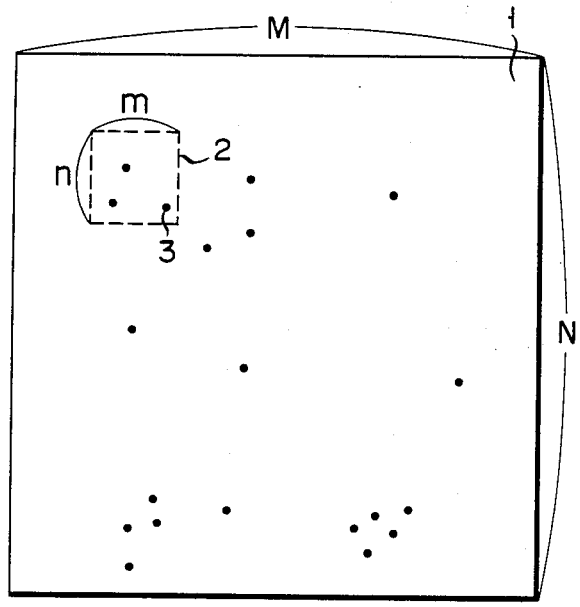
FIG. 1 is a diagram showing the relationship between an image in which objects to be inspected are irregularly distributed and a small region from which a feature is extracted.
Figure 2A:
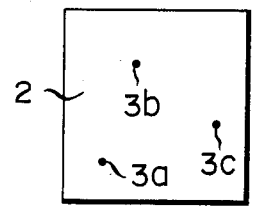
FIGS. 2A and 2B are diagrams for describing the problems in case where small regions are fixed.
Figure 2B:
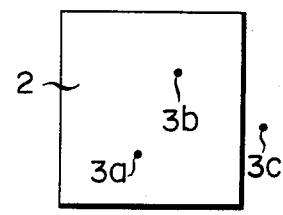

In this manner, the accumulated sum $\mathcal{S}_{i,j}$ of the picture element data of small region 2 which is defined by the position (i, j) of a new picture element is sequentially calculated every time new picture element data $d_{i,j}$ is read out by the two-dimensional scanning of image 1. Namely, according to the image processing as described above, small regions 2 are successively formed at an interval of one picture element for each row and column over the overall area of image 1 according to the two-dimensional scanning of image 1, and the accumulated sum of the picture element data in each small region is calculated. Therefore, the problem described with reference to FIGS. 2A and 2B can be solved.

Figure 4:
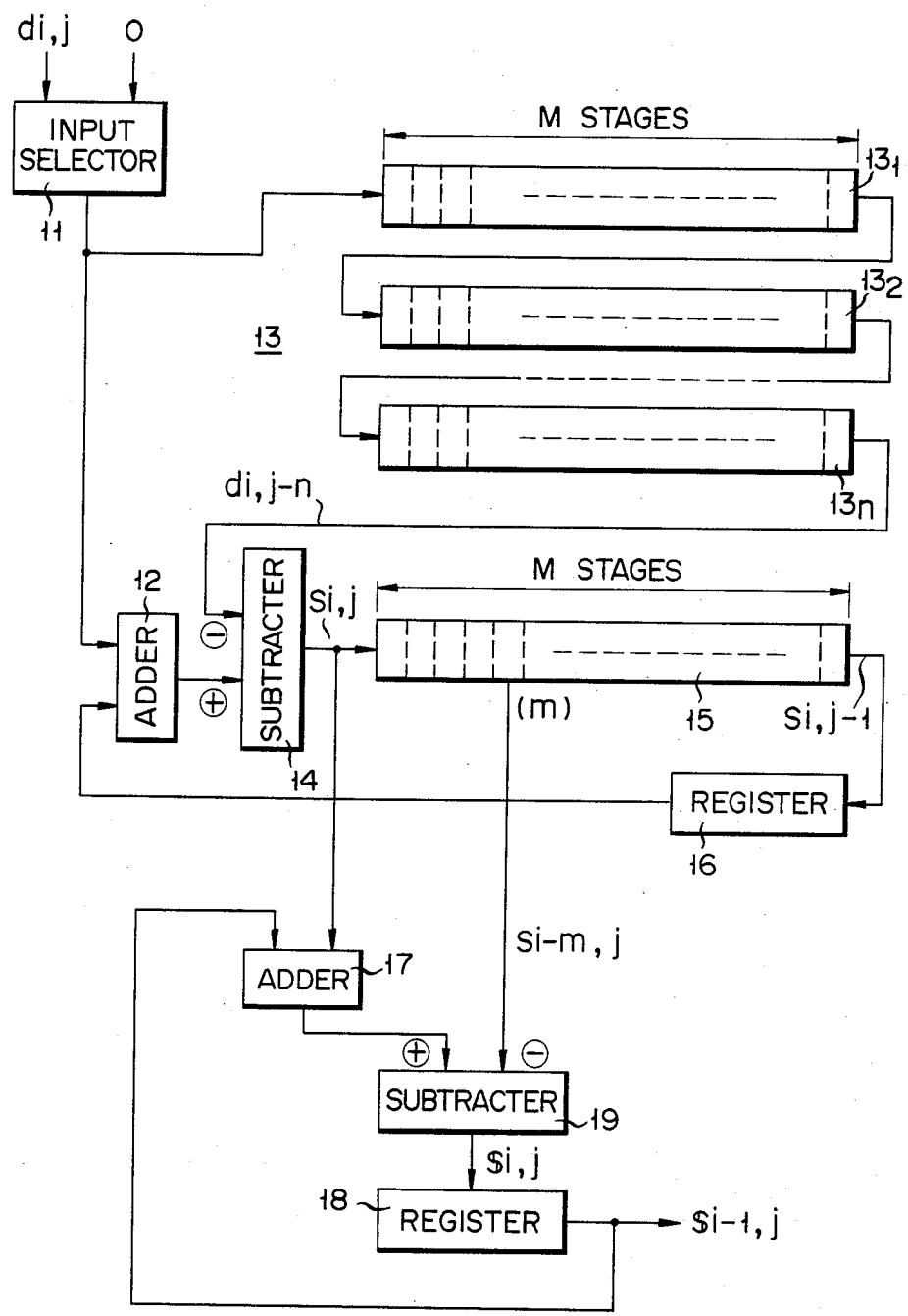
FIG. 4 is a block diagram of an image processing device according to one embodiment of the present invention.

A device for executing the above-mentioned calculation processing of picture element data will be described with reference to FIG. 4.

Picture element data which are temporarily stored in an image memory are read out serially by two-dimensional scanning. The picture element data $d_{i,j}$ thus read out is applied through an input selector 11 to an adder 12 and a first shift register 13 which operates as a memory and delay circuit. The shift register 13 has (M×n) stages in total, and may be considered as a series connection of n shift registers $13_1, 13_2, \ldots, 13_n$ each having M stages. As described above, M designates the number of picture elements in the row direction of image 1, and n is the number of picture elements in the column direction in small region 2. The data transfer in shift register 13 is effected by clock pulses which are synchronized with the read-out of picture element data from the image memory. The selector 11 inputs zero data prior to the read-out of data $d_{i,j}$ from the image memory, and resets the respective shift registers to zero.

The picture element data from shift register 13 which has been delayed by a period of n lines is applied to a subtracter 14 together with the output data of adder 12. The output data of subtracter 14 is applied to a second shift register 15 which has M stages and operates as a memory and one-line delay circuit. The output data of second shift register 15 is applied to adder 12 through a shift register 16 which operates as a temporary memory circuit. The shift register 15 stores the data sum of n picture elements in the respective M rows. The adder 12 adds new picture element data of each row to the data sum of n picture elements of the corresponding row stored in shift register 15, and the output of adder 12 represents the data sum of (n+1) picture elements of each row. The subtracter 14 subtracts the n-line delayed output data of shift register 13 from the output data of adder 12 which represents the sum of (n+1) picture element data of each row so that the data sum of new n picture elements of each row is provided.

The output data of subtracter 14 is fed to an adder 17 to be added to output data of a shift register 18. The output data of m-th stage of shift register 15 is applied to a subtracter 19 to be subtracted from the output data of adder 17. The output of subtracter 19 represents the accumulated sum $S_{i,j}$ of (m×n) picture element data of a small region which is defined by the position (i, j) of a picture element corresponding to the present input data $d_{i,j}$. The register 18 receives the output data of subtracter 19 to temporarily store it, and holds the accumulated sum $\mathcal{S}_{i-1,j}$ of picture element data in a small region defined by the position (i−1, j) before the input data $d_{i,j}$ is applied.

The operation of the image processing device thus arranged will be described. Initially, zero data is applied through selector 11 to first and second shift registers 13 and 15, thereby resetting the contents of these registers to zero. After shift registers 13 and 15 are reset, picture element data $d_{i,j}$ is input through selector 11. Thus, the data $d_{i,j}$ is sequentially stored in first shift register 13. At this time, since data which are sequentially read from shift register 13 all indicate zero, the picture element data of the first line is sequentially stored through adder 12 and subtracter 14 in shift register 15. When the picture element data of the next line is input, the output data of shift register 13 still indicate zero, and the picture element data before one line is read out of shift register 15, so that the data sums of picture elements of the respective rows on the first and second lines are sequentially applied through adder 12 to shift register 15. In this manner, data sums $S_{1,n}, S_{2,n}, \ldots, S_{M,n}$ of picture element data of n lines in the row direction are stored in the respective stages of shift register 15. Thereafter, when picture element data on (n+1)-th line is input, the n-line delayed picture element data are sequentially read out of shift register 13 to be applied to subtracter 14. Namely, the data of the n-line preceding picture element of a row is subtracted from the output data of adder 12 which exhibits the data sum of (n+1) picture elements of the corresponding row. Accordingly, to shift register 15 is input the data sum $S_{i,j}$ which is represented by the following equation as described above.

$$S_{i,j} = S_{i,j-1} + d_{i,j} - d_{i,j-n}$$

On the other hand, the data sum of n picture elements of each row is applied to shift register 18 through adder 17 from subtracter 14. Accordingly, the data sum of n picture elements are accumulated for each row. However, since the output data of the m-th stage of shift register 15 is applied through subtractor 19 to register 18, the data sum of m-row preceding n picture elements is subtracted every time the data sum of n picture elements of a new row is output from subtracter 17. Namely, in register 18 the data of (m×n) picture elements forming small region 2 are accumulated, and the accumulated sum is updated every time new picture element data is input, with the result that the accumulated sum of (m×n) picture element data is sequentially obtained every small regions displaced by one picture element.

In the embodiment described above, the picture element data may be a binary signal or multi-valued signal. The embodiment described above is suitable for the image processing at the image portion except the periphery of image 1. In other words it is preferred that, the image portion to be processed be not set to the entire region of image 1, but to a portion slightly smaller than the entire region of image 1.

Figure 5:
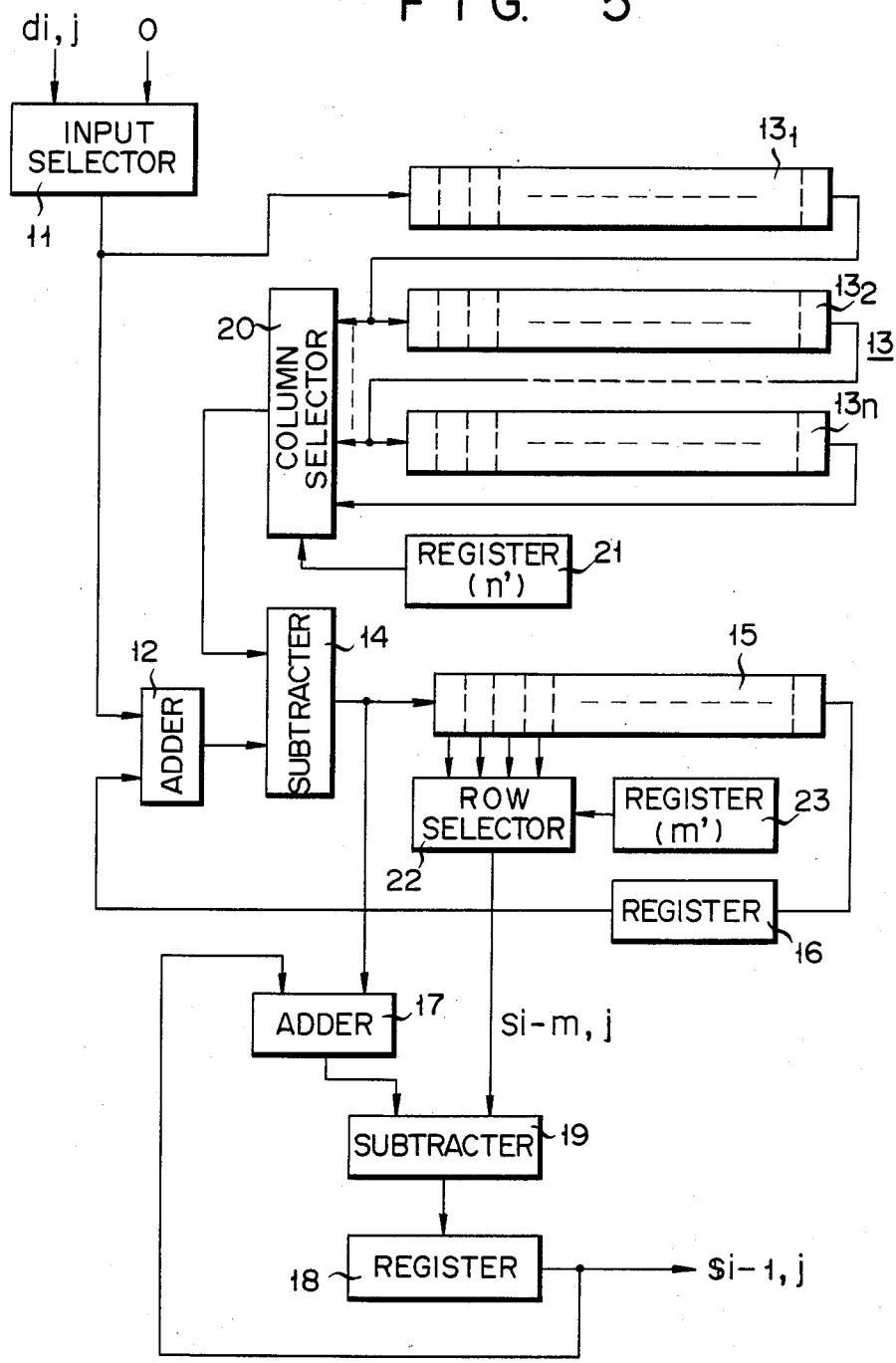
FIG. 5 is a block diagram of an image processing device according to another embodiment of the present invention.

A second embodiment of the present invention will be described with reference to FIG. 5. This embodiment is arranged to alter the size of small region 2. In FIG. 5 the same parts as those in FIG. 4 are designated by the same reference numerals and the description thereof will be omitted. A column selector 20 is provided between M-stage shift registers $13_1, 13_2, \ldots, 13_n$ and subtracter 18. This selector 20 selects one of shift registers $13_1, 13_2, \ldots, 13_n$ in accordance with a numerical value n' set in a register 21 and couples it to subtracter 14. Thus, the number n of the picture elements of small region 2 in the column direction can be selectively set. Further, a row selector 22 is provided to select one of a plurality of stage outputs of register 15 in accordance with a numerical value m' set in a register 23. Thus, the number m of the picture elements in row direction of small region 2 can be selectively set in accordance with the numerical value set in register 23.

The image processing device of the present invention is not limited to the embodiments described above. The shift register as a temporary memory may be replaced by a random access memory (RAM). The shift register may be reset directly by a reset signal instead of application of the zero data thereto. The alternation of the size of the small region may be performed merely by altering the number of the picture elements in either one of the row and column directions. Moreover, the small region may be tilted with respect to scanning lines and the tilted small region will be obtained by selectively altering the number of stages of the shift registers.

What is claimed is:

1. An image data processing device for extracting a feature of a small region of an image, comprising:
   first memory means connected to sequentially receive input picture element data obtained by two-dimensional scanning of the image of temporarily storing the data, said first memory means having (M×n) stages to temporarily store (M×n) picture element data on n scanning lines, the (M×n) picture element data stored being sequentially read out of said first memory means in the order of application of said picture element data to said first memory means;
   second memory means having M stages for temporarily storing data sequentially applied to an input thereof, the M data stored being read out of said second memory means in the order of application of data thereto;
   first arithmetic operation circuit means for effecting an arithmetic operation of the input picture element data plus the output data of said second memory means minus the output data of said first memory means and thereby producing output data that is coupled to the input of said second memory means;
   third memory means for temporarily storing data applied to an input thereof; and
   second arithmetic operation circuit means for effecting an arithmetic operation of the output data of said first arithmetic operation circuit means plus output data of said third memory means minus output data of m (<M)-th stage of said second memory means and thereby producing output data that is coupled to the input of said third memory means;
   means for changeably selecting one of multiples of M)-th stage of said first memory means and coupling, as the output data of said first memory means, output data of the selected stage to said first arithmetic operation circuit means; and
   means for changeably selecting one of a plurality of stages of said second memory means and coupling, as the output data of said second memory means, output data of the selected stage to said second arithmetic operation circuit means.

2. An image data processing data according to claim 1, wherein said input picture element data is a binary signal.

3. An image data processing device according to claim 1, wherein said input picture element data is a multi-valued signal.

4. An image data processing device according to claim 1, wherein said first memory means is a shift register having (M×n) stages.

5. An image data processing device according to claim 1, wherein said second memory means is a shift register.

6. An image data processing device according to claim 1, wherein said first and second arithmetic operation circuit means each have an adder circuit and a subtractor circuit.

7. An image data processing device for extracting a feature of a small region of an image, comprising:
   first memory means connected to sequentially receive input picture element data obtained by two-dimensional scanning of the image for temporarily storing data of (M×n) picture elements on n scanning lines, said means having a series connection of n first shift registers each having an output at which is produced output data, and each having M stages;
   first selecting means for changeably selecting one of the outputs of said first shift registers of said first memory means;
   second memory means having a second shift register having M stages;
   first arithmetic operation circuit means for effecting an arithmetic operation of the input picture element data plus output data of said second shift register minus output data of one of said first shift registers which is selected by said first selecting means and coupling output data to an input of said second register;

second selecting means for changeably selecting one of a plurality of stages of said second shift register;

third memory means for temporarily storing data applied to its input thereof; and second arithmetic operation circuit means for effecting an arithmetic operation of the output data of said first arithmetic operation circuit means plus output data of said third memory means minus output data of a stage of said second shift register selected by said second selecting means and thereby producing output data that is coupled to the input of said third memory means.

* * * * *